United States Patent
Delecrin et al.

(10) Patent No.: US 9,987,044 B2
(45) Date of Patent: *Jun. 5, 2018

(54) PLATE FOR OSTEOSYNTHESIS DEVICE AND METHOD OF PREASSEMBLING SUCH DEVICE

(71) Applicant: LDR Medical, Sainte-Savine (FR)

(72) Inventors: Joël Delecrin, Vertou (FR); Jérôme Allain, Paris (FR); Patrick Tropiano, Marseilles (FR); Serge Ganglof, Aplerin (FR); Rémi Poncer, Vannes (FR)

(73) Assignee: LDR Medical, Sainte-Savine (FR)

(*) Notice: Subject to any disclaimer, the term of this patent is extended or adjusted under 35 U.S.C. 154(b) by 0 days. days.

This patent is subject to a terminal disclaimer.

(21) Appl. No.: 15/414,523

(22) Filed: Jan. 24, 2017

(65) Prior Publication Data
US 2017/0196596 A1    Jul. 13, 2017

Related U.S. Application Data

(63) Continuation of application No. 14/584,674, filed on Dec. 29, 2014, now Pat. No. 9,549,766, which is a continuation of application No. 13/454,927, filed on Apr. 24, 2012, now Pat. No. 8,920,474, which is a continuation of application No. 10/492,827, filed as
(Continued)

(30) Foreign Application Priority Data

Oct. 18, 2001 (FR) ...................... 01 13460

(51) Int. Cl.
*A61B 17/70* (2006.01)

(52) U.S. Cl.
CPC ........ *A61B 17/7007* (2013.01); *A61B 17/701* (2013.01); *A61B 17/7011* (2013.01); *A61B 17/7037* (2013.01); *A61B 17/7041* (2013.01)

(58) Field of Classification Search
CPC ............ A61B 17/7082; A61B 17/7007; A61B 17/701; A61B 17/7011; A61B 17/7037; A61B 17/7041; A61B 17/864
USPC ........ 606/246, 250–253, 257–261, 264, 268, 606/271, 272, 276–281, 286, 287, 300, 606/301, 305–308, 319–321
See application file for complete search history.

(56) References Cited

U.S. PATENT DOCUMENTS

| 8,162,988 B2* | 4/2012 | Delecrin | A61B 17/7007 606/266 |
| 8,221,457 B2* | 7/2012 | Delecrin | A61B 17/7007 606/246 |

(Continued)

*Primary Examiner* — Pedro Philogene
*Assistant Examiner* — David C Comstock
(74) *Attorney, Agent, or Firm* — Lauff Law PLLC

(57) ABSTRACT

Various methods, devices, and systems are disclosed that facilitate easier and more compact implantation of osteosynthesis devices. In some embodiments, implants are screwed into two vertebrae and a plate is used to hold and displace the spine. In some plate embodiments, at least one longitudinally elongated opening is disposed at one end of the plate and partially opening onto an edge of the plate. In some plate embodiments, at least one longitudinally elongated opening is disposed at one end of the plate having a portion sufficiently large to be inserted without disassembly in the fixation means of an implant already screwed into the spine when the fixation means are already assembled.

20 Claims, 8 Drawing Sheets

Related U.S. Application Data application No. PCT/IB02/04307 on Oct. 18, 2002, now Pat. No. 8,162,988.

(56) References Cited

U.S. PATENT DOCUMENTS

| | | | |
|---|---|---|---|
| 8,920,474 B2 * | 12/2014 | Delecrin ............ | A61B 17/7007 606/257 |
| 9,549,766 B2 * | 1/2017 | Delecrin ............ | A61B 17/7007 |

* cited by examiner

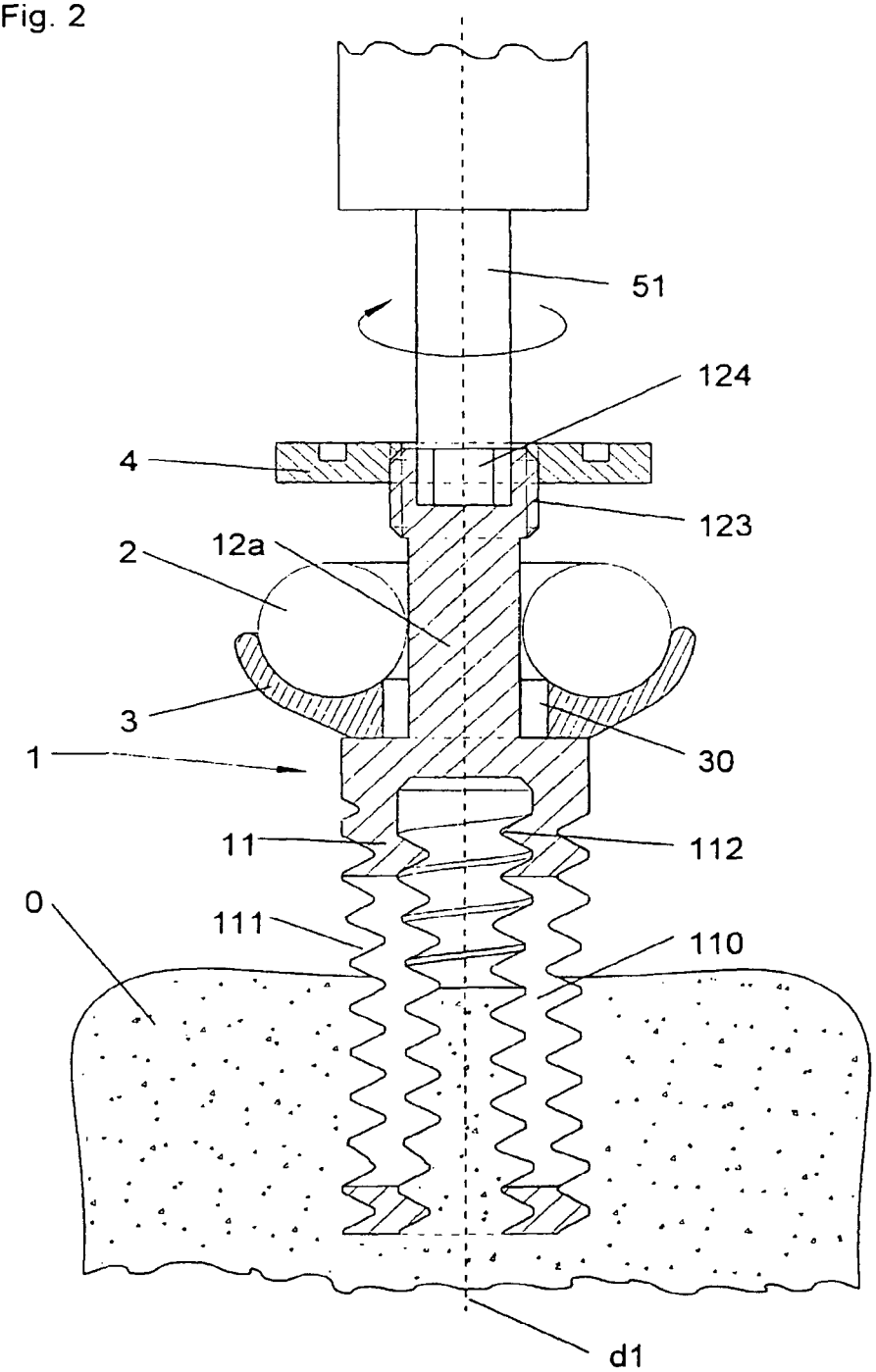

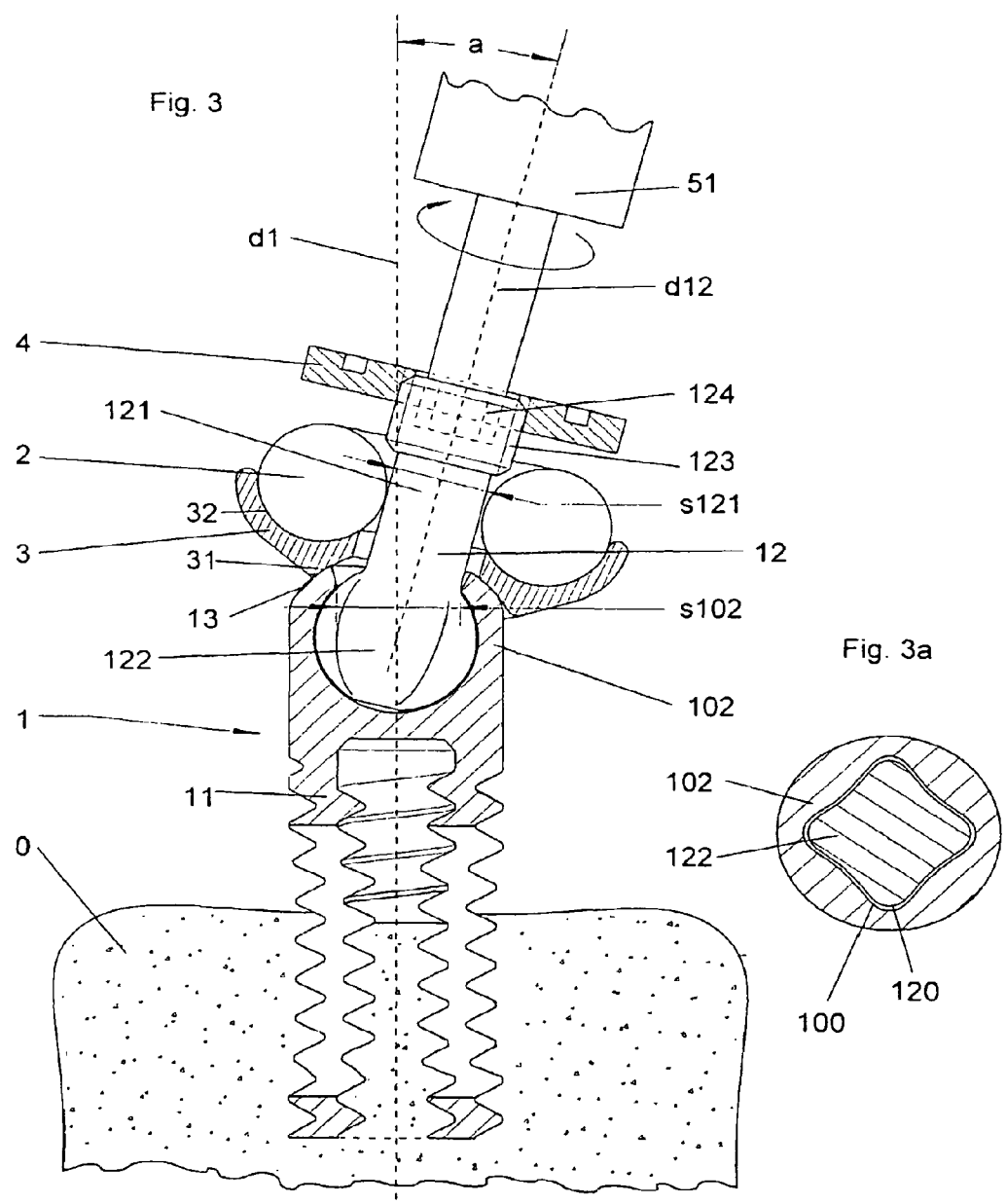

PLATE FOR OSTEOSYNTHESIS DEVICE AND METHOD OF PREASSEMBLING SUCH DEVICE

CROSS-REFERENCE TO RELATED APPLICATIONS

This application is a continuation of U.S. patent application Ser. No. 14/584,674 filed Dec. 29, 2014, and issuing as U.S. Pat. No. 9,549,766 on Jan. 24, 2017, which is a continuation of U.S. patent application Ser. No. 13/454,927 filed Apr. 24, 2012, and issuing as U.S. Pat. No. 8,920,474 on Dec. 30, 2014, which is a continuation of U.S. patent application Ser. No. 10/492,827 filed Oct. 18, 2002, as International Application No. PCT/IB02/04307 and entering the National Stage in the United States with a 371(c) date of Jul. 15, 2004, and issuing Apr. 24, 2012, as U.S. Pat. No. 8,162,988. This application claims priority under 35 U.S.C. 119 to French Patent Application No. 01 13460, filed in FRANCE on Oct. 18, 2001, through U.S. patent application Ser. No. 10/492,827; U.S. patent application Ser. No. 13/454,927; and U.S. patent application Ser. No. 14/584,674.

BACKGROUND

The present invention relates to an osteosynthesis device, particularly for spinal support or correction, enabling easier and compact implantation, that can be particularly used in the case of implantation via the anterior approach, and a preassembly method for such a device.

For spinal support or correction, a device comprising a supporting element comprising one or more support bars or plates positioned along the spinal column is used, and fixed to certain vertebrae by implants. Said implants are fixed at one end to the plate and at the other end to the vertebrae by bone anchorage means, for example a threaded part screwed inside the actual vertebra.

In such devices, it is known to use a plate comprising several holes, to join the implants fixed to several vertebrae, as described in the patent FR2726171, for example. Said bars then surround or pass through the head of the screw and are locked with a nut screwed onto said head.

However, such a device requires that the clamping nut only be fitted on the screw after the screws and the plate have been positioned. Therefore, said nut can only be inserted onto the screw head during the operation, with all the difficulties and risks of loss that may be caused by handling and assembling a small part inside a human body. This operation is all the more problematic when said operation is conducted by means of endoscopy, for example when it is necessary to implant via the anterior approach, i.e. via the front of the body or on the front face of the spine.

A device according to the prior art also requires that the implants be fixed and completely clamped before the plate is positioned. Therefore, in the event of delicate operative conditions, it is difficult to successfully position the plate very close to the spine. This problem arises for example when the shape of the spine comprises too many irregularities, due to spinal displacement or deformation or in the presence of outgrowths such as osteophytes. There are similar problems in the case of implantation by the anterior approach, i.e. via the front of the body or on the front face of the spine. Indeed, the anatomical conditions in this case frequently only leave space for a compact size. In addition, it is often necessary to work by means of endoscopy in this case, which renders the operation difficult and gives a less satisfactory view of the implant insertion depth.

In some cases, to enable subsequent consolidation of the fixation between the implant and the vertebra, an implant composed of a so-called "rehabitable" screw is used, i.e. a hollow screw wherein the inside communicates with the outside via openings passing through the threaded wall. During the screwing into the vertebra, part of the bone substance penetrates inside the screw. Over time, the bone substance fuses between the inside and outside of the screw via these openings, thus forming consolidation over time.

In this way, the patent FR 2726171 discloses a hollow screw wherein the openings are produced by cutting on the inner surfaces of said screw longitudinal grooves which cut into the base of the outer threading. However, during positioning or subsequently, such a screw may form anchoring which is not sufficiently strong and is liable to be dislodged or torn from the vertebra wherein it is implanted.

BRIEF SUMMARY

One of the aims of the invention of the invention is to provide a plate that can be fitted on preassembled implants already screwed into the spine.

Another aim of the invention is to provide an osteosynthesis device that can be partly preassembled before the operation to enable easier implantation.

In this way, the invention relates to a device as described above, wherein the plate has an elongated shape and comprises, on at least one of its ends, at least one longitudinally elongated opening. The opening has at least one part opening onto an edge of the plate, or one part of a sufficiently large size as to be inserted without disassembly in an attachment structure of an implant that had been previously screwed into the spine when said attachment structure are already assembled. The opening also has one part having a substantially constant width and that is able to slide longitudinally in the attachment structure of said implant after having been inserted and of being disposed thereon. Such a plate can thus be assembled by disposing one end to an already fitted implant, and then sliding in the attachment structure of said implant to insert the other end in another already fitted implant. The plate is then again slid to bring both ends into the attachment position. The attachment structure of the two implants were assembled before being attached to the spine.

One aspect of this invention constitutes an osteosynthesis device having a plurality of implants that are each adapted to be joined to one or more vertebrae. When thus joined to a vertebrae, these implants a substantially rigid point of attachment between the implanted vertebrae and at least one support element. The support element is made up of at least one plate or bar. The assembly of the supporting element(s) and the implants are adapted to hold a spine in place, or to displace a spine from an improper alignment into a more correct alignment. The supporting element(s) is joined to at least two of the implants by an attachment structure. The supporting element has an elongated shape wherein at least one of its ends has at least one longitudinally elongated opening. At least one opening extends to an edge of the plate, or is an aperture of a sufficiently large size to accept the insertion of the exposed part of the implanted attachment member which is sized to be able to be inserted, without disassembly, to the support member through the hole. In this arrangement, the implant that has previously been attached to a vertebrae of the spine. A part of the aperture has a substantially constant width that is able to slide longitudinally on to the attachment structure of the implant after the implant has first been inserted and of fixed to the support structure. One end of the support plate is adapted to be assembled at one end to first implant that has been attached to a vertebrae, and is adapted to then be caused to slide in relation to the attachment structure of the first implant so as to enable the other end of said plate to be attached to a second implant that has previously been joined to a vertebrae (preferably a different vertebrae), and is adapted to then be slid again in order to bring both ends of said plate into attachment to the respective attachment structures.

According to one embodiment, the plate comprises two parts having identical lengths or not. The two parts are joined together by a joining part that is located in an inner part of the plate, i.e. at a sufficient distance from the plate ends to enable the plate to be attached onto two implants so that one implant is on each side of said joining part.

According to one embodiment, the joining part is located in a position offset with respect to the center of the plate length.

According to one embodiment, the plate has an "H" or "h" shape.

According to one embodiment, the plate has at least one longitudinally elongated opening having a first constant width region and a second region that is larger in size than the first region. The opening is large enough to allow the attachment structure of an implant to pass through the plate before sliding to bring the attachment structure into the first region.

Another aim of the invention is to propose a compact osteosynthesis device, that can be fitted and adjusted in a position very close to the spine.

This aim is achieved by an osteosynthesis device, particularly for the spine, comprising a plurality of implants that can be screwed into one or more vertebrae and provide a rigid joint between said vertebrae and at least one plate or bar used to hold or displace the spine, characterized in that the plate is joined to at least one implant by fixation means able to hold said plate without preventing the implant from rotating on its screwing axis, or without preventing a specified clearance of the plate with respect to the implant, or both: thus making it possible to continue screwing the implant, or adjust the position of the plate, or both, after the plate has been assembled on the implant.

According to one embodiment, at least one implant has an elongated shape around an axis, referred to as the implant axis, and comprises a first bone anchoring end bearing at least one threading and a second end with an elongated part passing through a plate support, said plate support being free in rotation around said elongated part, said elongated part bearing clamping means able to hold and clamp the plate against said plate support.

Another aim of the invention is to propose an osteosynthesis device that can be screwed or clamped when it is not possible to use a tool in the actual axis of the implant.

This aim is achieved by a device as described above, characterized in that the elongated part, referred to as the clamping support, of the implant is mobile with respect to the rest of the implant, along a universal type joint between a part of the implant referred to as the screw head and a part of the clamping support referred to as the support head, thus making it possible to continue screwing the implant after the plate has been assembled on the implant, by rotating the clamping support around a clamping support axis, when said axis forms a non-null angle with the axis of the implant.

According to one embodiment, the plate surrounds the clamping support or the second end of the implant at least partly and rests on a surface of its complementary plate support, said plate support having on the implant side a concave surface in the form of a spherical portion which is supported in a complementary fashion on the outer surface of the implant screw head.

According to one embodiment, the clamping support has a first elongated end along the support axis and a second end bearing the support head, said support head having a non-circular cross-section having at least one concave part and comprising at least one dimension greater than at least one cross-section of the first end of the clamping support; said support head having firstly one section roughly partly circular along a plane including the support axis, and being secondly arranged in the screw head inside a housing wherein the inner surface has at least one projecting part cooperating with the concave part of the support head to prevent rotation of the clamping support around its axis.

According to one embodiment, the inner surface of the screw head housing has a shape substantially complementary to the outer surface of the support head.

According to one embodiment, the housing receiving the support head has, on the side of said clamping head, a specified dimension to allow the clamping support a clearance along a specified angle, between the axis of the clamping support and the axis of the implant, without said clamping support escaping from said housing.

According to one embodiment, the clamping support head has a star-shaped cross-section with rounded ends, along a plane perpendicular to the support axis.

According to one embodiment, the clamping support clamping means comprise a threading that is adapted to cooperate with a nut to hold or clamp the plate against the plate support.

According to one embodiment, the clamping support comprises at its end opposite the implant an inner or outer recess capable of receiving a rotational drive tool and thus enable the complete screwing or clamping of the implant in the vertebra.

One of the aims of the invention is to propose an osteosynthesis device enabling improved screw implantation strength, during fitting, during the period prior to bone fusion or after consolidation.

This aim is achieved by a device such as that described above, characterized in that the first bone anchorage end of at least one implant has a longitudinal bore concentric to its outer surface, said bore communicating with the outside by at least one bone fusion opening disposed in the wall between said inner bore and said outer surface, thus enabling a fusion of the bone substance in contact with said first end, between the inside and the outside.

According to one embodiment, the first bone anchorage end of at least one implant has two threadings that wind in the same direction during the screwing of the implant. These are borne respectively by the outer surface of said first end and the inner surface of the bore that it comprises.

According to one embodiment, at least one bone fusion opening has the shape of a longitudinal oblong hole.

Another aim of the invention is to provide a preassembly method for such an osteosynthesis device.

This aim is achieved by the preassembly method for a device according to the invention, characterized in that it comprises the following steps:

assembly of the plate support on the clamping support of an implant; and assembly of the nut on the threading of the clamping support of said implant.

BRIEF DESCRIPTION OF THE SEVERAL VIEWS OF THE DRAWINGS

The invention, with its characteristics and advantages, will be seen more clearly upon reading the description with reference to the appended figures wherein:

FIG. 2 represents a longitudinal section view of an implant of a device according to the invention in the implant clamping phase after insertion of the plate, in an embodiment comprising a plate support free to rotate around a rehabitable hollow screw implant and fixed clamping support;

FIG. 3 represents a longitudinal section view of an implant of a device according to the invention in the implant clamping phase after insertion of the plate, in an embodiment comprising a plate support free to rotate around a rehabitable hollow screw implant and inclinable clamping support;

FIG. 3a represents a partial view of an implant according to the invention, in a section along a plane passing through the center of the support head and perpendicular to the support axis;

DETAILED DESCRIPTION

Figure 1A:
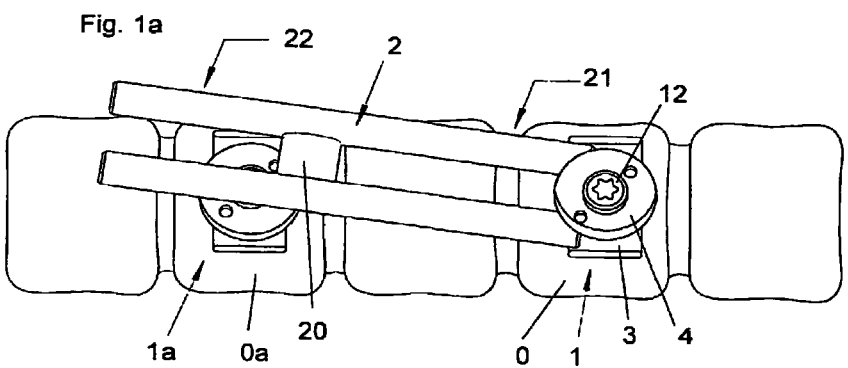
FIGS. 1a, 1b, and 1c represent an osteosynthesis device according to the invention in an embodiment comprising an "H"-shaped plate and two polyaxial head implants fitted on an interval vertebra, in three successive phases of the fitting of the plate in the implants.

In an embodiment represented in FIG. 2, the device according to the invention comprises an implant 1 comprising a first end 11 equipped with an outer threading 111, and is illustrated after a first having been screwed in the bone substance of a vertebra 0, after insertion of a plate 2 and during the final approach. Said first end 11 also comprises a cavity or an inner bore, itself equipped with an inner threading 112 wherein the screwing direction is the same as that of the outer threading 111. During the screwing of the implant into the vertebra 0, part of the bone substance tends to fill said cavity and is assisted therein by the action of the inner threading. Preferentially, the inner threading 112 and the outer threading 111 are of the same pitch, so as to minimize the strain exerted on the bone substance at the entry of the bore during screwing.

The wall between the inner cavity and the outside of the implant has one or more openings, referred to as bone fusion holes 110, in its part which is inside the vertebra after the attachment of the implant. In the time period following the implantation, generally approximately six months, the bone substance present outside and inside the implant tends to fuse. The fusing produced in this way improves the strength of said implantation, both by means of blocking via the bone fusion holes 110, and by means of cooperation of the inner threading 112 with the bone pin formed in this way.

In one alternative embodiment, the inner threading 112 has a greater pitch than that of the outer threading 111. During the screwing of the implant 1, the bone substance present inside the cavity is then attracted slightly more quickly than the implant progresses in the vertebra 0. This effect may make it possible to compensate for a filling defect liable to occur, for example by compression of the bone substance inside the bore. This effect may also make it possible to obtain more complete or more compact filling of said cavity, for example in order to obtain a specific compression or better filling of the cavity or the bone fusion holes 110, and thus favor bone substance fusion.

At its second end, i.e. the end opposite the vertebra, the implant 1 comprises an attachment structure that is used to insert, hold and finally clamp a bar or a plate 2. Said second end also comprises a receptacle for a drive means, using a tool of known type, such as a hexagonal recess 124.

Said structure comprises for example an elongated part 12a of a cross-section less than the central part of the implant, comprising a shoulder. Said elongated part 12a passes through a plate support 3 resting on said shoulder, and comprises at its end a threading 123 to receive a clamping nut 4. In one embodiment, said plate 2, as shown in FIG. 5a, is roughly "H"-shaped, comprising for example two cylindrical bars joined at their center by a rigid distance sleeve. In an alternative embodiment, the two bars are joined by a non-rigid joint. Because the joint is not rigid, it allows more latitude in the positioning of the plate. Said plate 2 is inserted between the plate support 3 and the nut 4, so as to surround the elongated part 12a of the implant. Once the plate is in position, the nut 4 is fastened, by hand or using a tool of a known type 52, FIG. 4, and cooperates with the threading 123 to clamp the plate 2 against the plate support 3 and thus lock the assembly.

In said embodiment, the plate support 3 comprises a bore 30 with a substantially rectangular insert passing through its center. Said plate support 3, on the side of the plate, has one or more surfaces 2 that are substantially complementary to the surface of the plate 2 resting on them. In said embodiment, the central bore of the plate support 3 is sufficiently larger than the part 12a passing through it to allow a clearance of said support 3 transversally and at an angle with respect to the axis d1 of the implant. Said clearance makes it possible to adjust the relative position of the plate supports of two implants 1, 1*a* easily, and thus insert the plate 2 easily even if the implants are not well aligned or in the event of a relatively inaccessible anatomical environment. According to an alternative embodiment not shown, the plate support receives a plate 2*a*, FIG. 5*b*, comprising a single bar at one of its ends. Said plate support can then comprise an offset bore instead of the central bore 30, without departing from the scope of the invention.

Since the plate support 3 is free to rotate around the part 12*a* of the implant 1, it is clearly understood that it is possible to continue screwing said implant into the vertebra 0, even when the plate is already in position, provided that the attachment structure is not firmly fastened on said plate 2. In this way, by inserting the plate 2 into said attachment structure before the implant 1 is entirely screwed on, it is possible not to be hindered by the various differences in levels or outgrowths liable to be present in the immediate vicinity of the spine. Once the plate is held in place but not clamped, it is still possible to finish screwing the implant into the vertebra, by rotating it via an opening of the plate support 3. The attachment structure then holds the plate 2 close to the spine, the screwing of the implant providing sufficient force to oblige the plate to come closer to the spine. Therefore, the plate can be positioned and inserted with little effort, while being positioned definitively very close to the surface of the vertebra, which makes it possible to obtain a compact device size once fitted.

Figure 4:
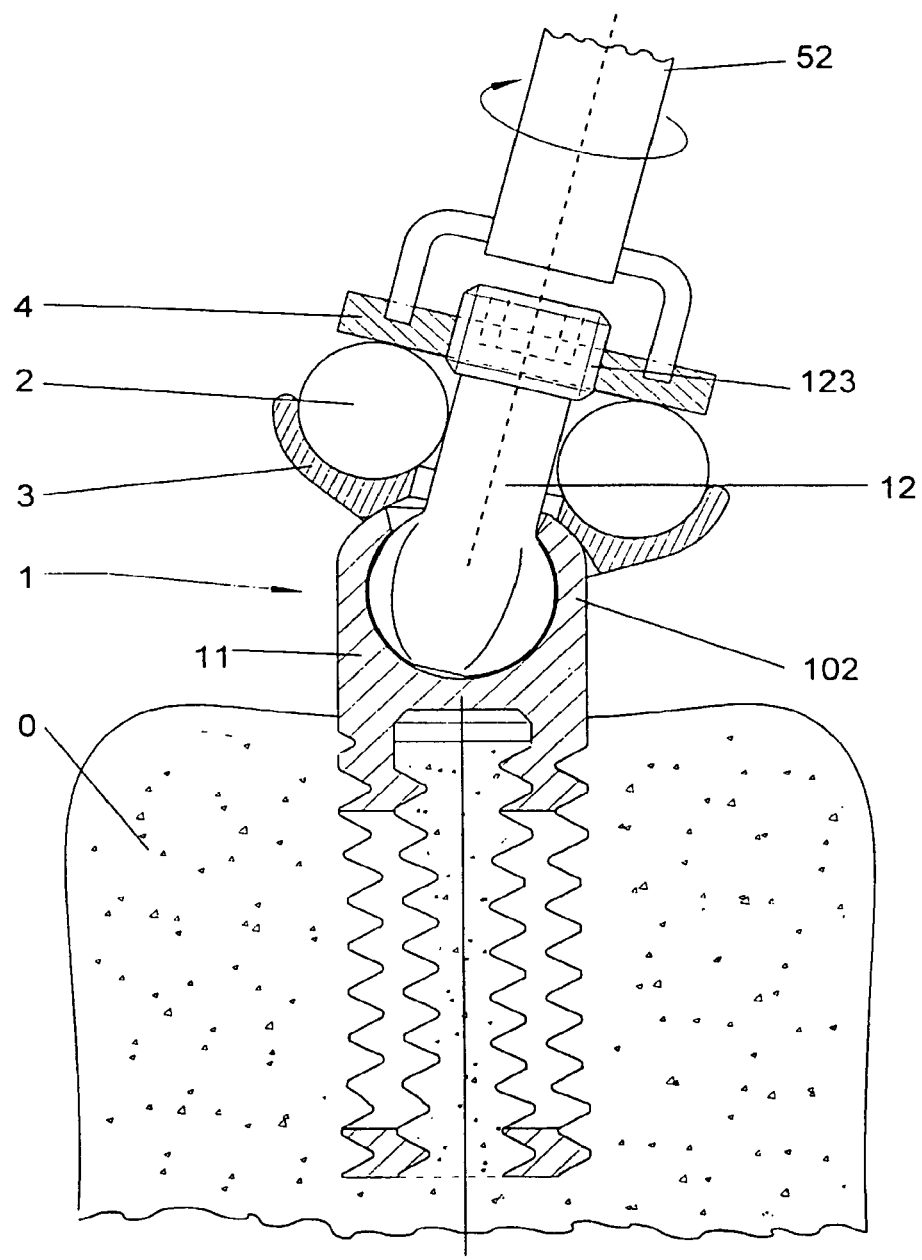
FIG. 4 represents a longitudinal section view of an implant of a device according to the invention in the plate clamping phase once the implant is in its definitive position, in an embodiment comprising a plate support free to rotate around a rehabitable hollow screw implant and inclinable clamping support.
Figure 5:
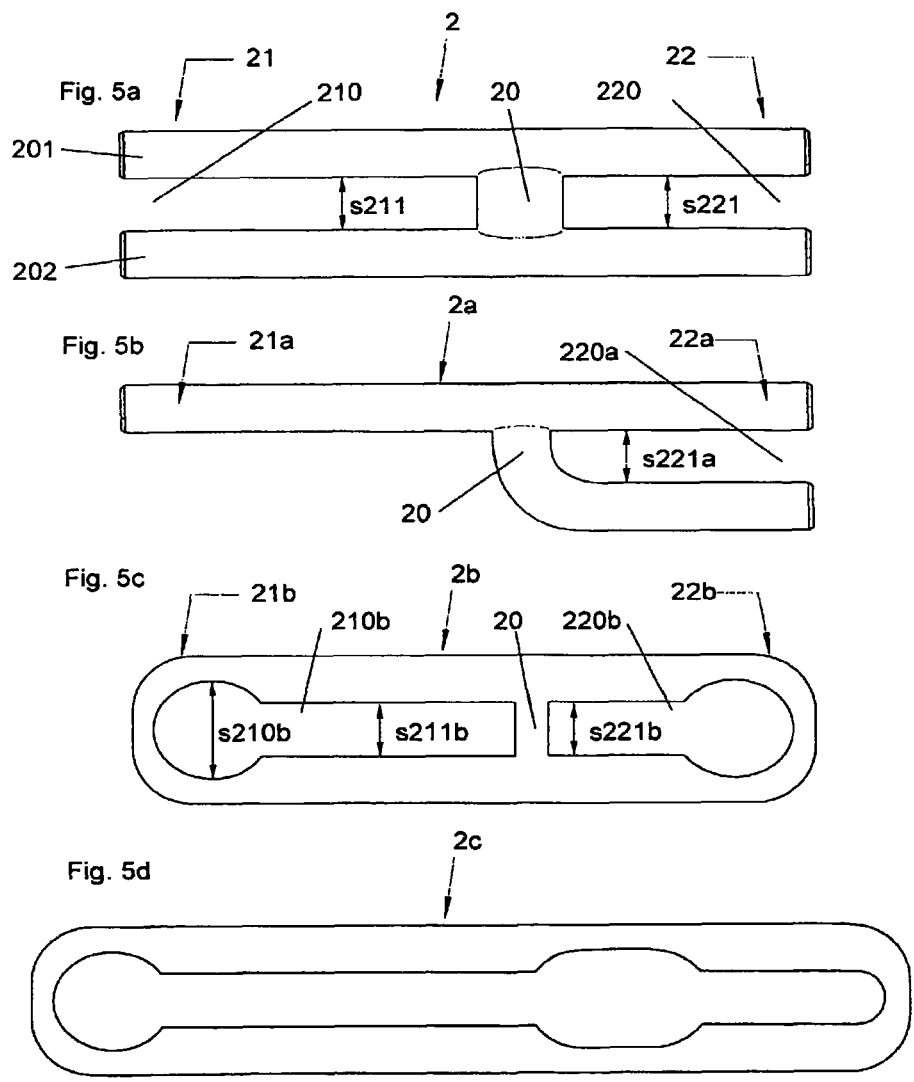
FIGS. 5a, 5b, 5c and 5d represent a top view of a plate of a device according to the invention, in an embodiment comprising a plate which is respectively "H"-shaped with two through openings, "h"-shaped with one through opening, with two non-through openings and with one non-through opening.

In a preferential embodiment of the device according to the invention, represented in FIGS. 3, 3*a* and 4, the implant 1 comprises a mobile part, referred to as the clamping support 12, at its second end opposite the first end 11 screwing into the vertebra 0. Said clamping support 12 has an elongated first end 121 along a support axis d12. Said elongated end passes through the central bore of the plate support 3 and bears a threading 123 adapted to receive the clamping nut 4.

At a second end opposite its elongated end 121, the clamping support 12 bears a part, referred to as the support head 122, joining said clamping support 12 to the implant by its second end, referred to as the screw head 102, opposite the end 11 screwed into the vertebra 0. Along a plane perpendicular to the support axis d12, said clamping support head 122 has at least one dimension s122; FIG. 3*a*, greater than at least one cross-section s121 of the elongated end 121 of said clamping support 12. Said support head 122 is retained in a housing provided in the screw head 102 of the implant 1. For this purpose, said housing has an opening of a specified size s102 so as to retain the support head 122 inside said housing, while allowing a clearance of a specified angle a between the support axis d12 and the implant axis d1.

Said angular clearance of the clamping support 12 with respect to the implant enables angular and lateral movements facilitating the insertion of the plate in the fixation means of the implant, as described below. Said angular clearance also makes it possible to compensate for any alignment defects between the different implants 1, 1*a*; FIG. 1*c*, of a device according to the invention and therefore renders the positioning of the plate 2 in the attachment structure of said implants less delicate.

In said preferential embodiment, the plate support 3 rests on the screw head 102 of the implant 1, by means of a lower surface 31 that has at least a partially spherical surface for example. Said lower surface 31 of the plate support is in complementary contact with an upper surface 13 of said screw head. Said spherical complementary contact allows freedom of rotation and inclination of the plate support 3 with respect to the implant 1. Said spherical complementary contact of said surfaces 13, 31 also enables a uniform and stable support of said surfaces with respect to each other, after the plate 2 has been clamped onto the plate support, irrespective of the definitive angular position of said plate support 3 or the clamping support 12.

The implant 1 is screwed into the vertebra 0 by means of rotationally driving said implant by rotating the clamping support 12 around its own clamping axis d12. Said clamping support is rotated for example by a tool, of known type, inserted into at least one recess 124 contained in the elongated end 121 of said clamping support. The clamping support 12 preferably rotates the implant 1 by means of a universal type joint, i.e. the rotation of either of the two components around its axis rotates the other component around its own axis, the angle between the two axes possibly being non-null.

Said universal joint is produced by the cooperation of the outer surface 120 of the support head 122 with the inner surface 100 of the housing of the screw head 102 of the implant 1. Along a plane perpendicular to the support axis d12, the support head 12 has a section with a non-circular outline, for example in the shape of a star or cross with rounded corners, as illustrated in FIG. 3*a*. The housing of the screw head 102 which receives the support head 122, then has an inner surface 100 in substantial complementary contact with the outer surface 120 of said support head 122, said two surfaces 100, 120 cooperating to form the rotational joint between these two components 102, 122. The angular variation is allowed by the fact that the support head 122, and its complementary housing, have a section with a circular outline along at least one plane including the clamping support axis d12, or the implant axis d1, or both.

Figure 7A:
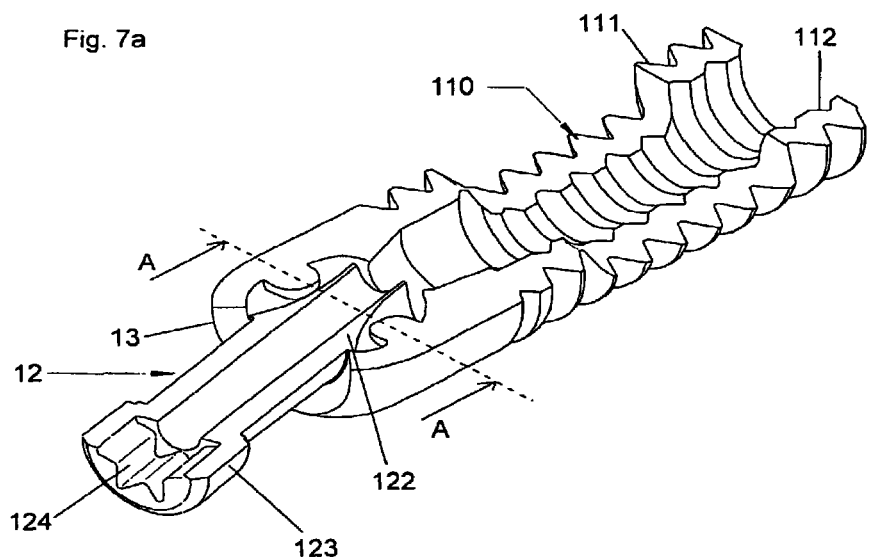
FIG. 7a represents a perspective view of a longitudinal section of an implant of a device according to the invention, in an embodiment comprising an inclinable clamping support and a rehabitable hollow screw with two oblong holes and according to an alternative embodiment where the screw head housing and the support head interact without being complementary in shape.
Figure 7B:
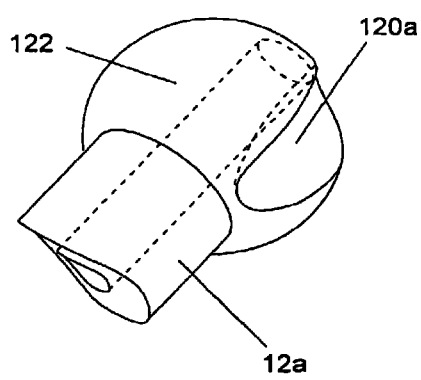
FIG. 7b represents a partial perspective view of the support head of an implant of a device according to the invention in the same alternative embodiment.
Figure 7C:
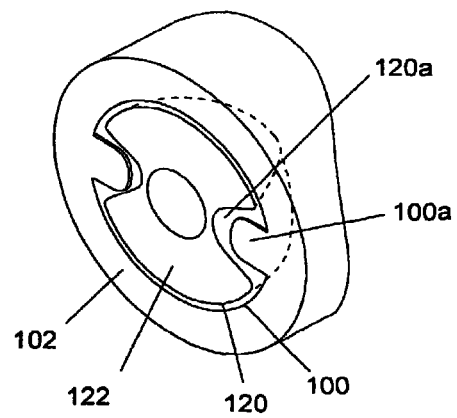
FIG. 7c represents a partial perspective view of a cross-section along the plane AA (as shown in FIG. 7a) of an implant of a device according to the invention in the same alternative embodiment.

According to an alternative embodiment illustrated in FIGS. 7*a* to 7*c*, the inner surface 100 of the screw head housing receiving the support head simply has one or more projecting parts 100*a*, for example two. The outer surface 120 of the support head 122 then has one or more concave parts 120*a* with which the projecting parts 100*a* of the screw head housing cooperate to prevent the rotation of the clamping support 12 around its axis d12.

In this way, it is clear that it is possible to continue screwing the implant 1 into the vertebra 0, after the plate 2 has already been inserted between the clamping nut 4 and the plate support 3, by adjusting the elongated end 121 of the clamping support 12 that is accessible via the nut 4. Since the plate support 3 is free to rotate with respect to the implant 1, said implant can rotate during screwing while leaving the plate 2 and the plate support 3 immobile.

Once the implant 1 is completely screwed into the vertebra 0, as illustrated in FIG. 4, the plate 2 can then be adjusted and locked in its definitive position, by tightening the clamping nut 4. Said nut may be tightened by hand, for example on a knurled part of its outer surface on the support axis d12, or using a tool 52 of known type, for example by adjusting two inner or outer recesses on the nut.

Figure 8:
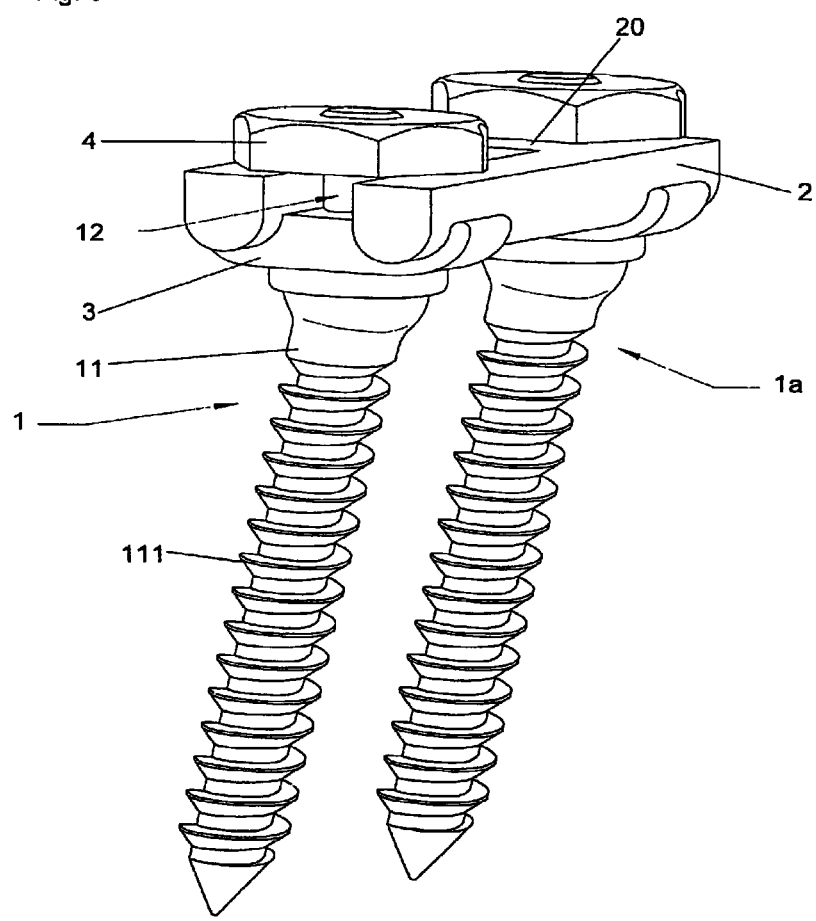
FIG. 8 represents an osteosynthesis device according to the invention in an embodiment comprising an "H"-shaped plate and two polyaxial head implants according to an alternative embodiment where the implants only comprise a single threaded part, on their outer surface.

According to an alternative embodiment illustrated in FIG. 8, a device according to the invention uses such implants but wherein the end 11 intended to be anchored in the vertebra only comprises one outer threaded part 111. In said alternative embodiment, the implant may comprise a longitudinal bore passing through it from one end to another, to enable positioning by means of sliding around a pin that has previously been implanted in the vertebra.

Several implants according to various alternative embodiments in the same device can of course be combined without departing from the scope of the invention.

Depending on the applications, in order to join two implants 1, 1*a*; FIG. 1*c*, it is possible to use a plate of different configurations, for example such as those represented in FIGS. 5*a*, 5*b*, 5*c* and 5*d*.

Figure 1B:
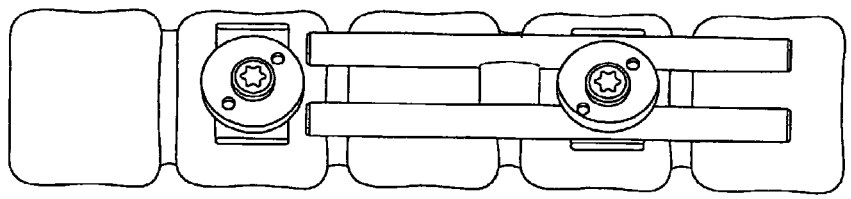
Figure 1C:
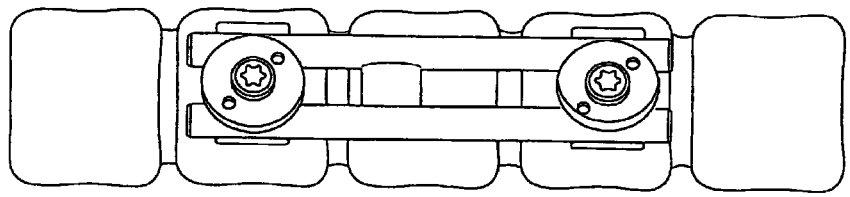

In the example of an embodiment illustrated in FIGS. 1*a*, 1*b*, and 1*c*, two implants 1, 1*a* are screwed into the body of two, respective, vertebrae 0, 0*a* respectively of the spine, spaced at an interval of one vertebra. These two implants are then fixed together by a plate 2 inserted into their attachment structures around the clamping support and then clamped between the plate support and the nut of each of said implants.

In the preferential embodiment represented in FIG. 5*a*, the plate 2 is elongated in shape and comprises two roughly parallel bars 201, 202, which are for example cylindrical, joined together in a rigid or flexible manner by a joining part 20. Said joining part joins the two bars at an inner part of the plate, i.e. at a specified non-null distance from each of the ends 21, 22 of the plate. More specifically, said joining part is located at a sufficient distance from each end of the plate so that said end can be inserted into the fixation means of an implant, and possibly slide in said attachment structure. The position of said joining part 20 may be located at the center of the plate, or be offset to allow a greater clearance for sliding during insertion as explained below.

At each end 21, 22 respectively, of the plate 2, the space between the two bars forms an opening 210, 220 respectively, opening out onto the edge of the plate. Said openings have a substantially constant transverse gap s211, s221, enabling longitudinal sliding of the plate in the attachment structure of an implant 1, 1*a*. This substantially constant transverse gap also makes it possible to clamp said attachment structure in any part of said openings 210, 220. Since said openings open onto the edge of the plate, it is possible to insert each of the ends of the plate into the attachment structure of an implant 1, 1*a* as illustrated in FIG. 1*a*, without having to remove the nut 4 if it was preassembled beforehand. At each end, this insertion consists of sliding the end of the two bars between the nut 4 and the plate support 3 of the implant 1, at either side of the clamping support 12.

In another embodiment represented in FIG. 5*b*, the plate 2*a* is elongated in shape and comprises a first end 21*a* comprising a single bar, which is cylindrical for example. Said first end can be inserted into an implant according to the prior art or into an implant as described in the present invention, for example in an alternative embodiment (not shown) where the plate support only comprises a single surface 32 in contact with the plate. The plate 2*a* also has a second end 22*a* comprising two substantially parallel bars, which are cylindrical for example. These two bars together form a longitudinally elongated opening 220*a*, of a roughly constant width s221*a*. Either of the two ends of said plate 2*a* can be inserted, or slid, or both, in the attachment structure of an implant according to the invention, in the manner described in the preferential embodiment.

In another embodiment represented in FIG. 5*c*, the plate 2*b* is elongated in shape and comprises a first end 21*b* having at least one opening 210*b* and a second end 22*b* having at least one second opening 220*b*, at least one of these openings not opening onto the edge of the plate 2*b*. These two openings 210*b*, 220*b* have a longitudinally elongated shape, i.e. along the length of the plate, and may be separated by one or more joining parts 20. These two openings have a substantially constant width s211*b*, s221*b*, and can be positioned by means of sliding and then be clamped in the attachment structure of the implants. At least one of said openings has a part, referred to as a notch, of a larger size s210*b*, s220*b*, of a shape and size able to allow the nut 4 of the attachment structure of an implant to pass through. Therefore, such a bar 2*b* can also be inserted in the attachment structure of an implant 1 when said attachment structure is already assembled, therefore not requiring handling of small parts, such as the nut 4 or the plate support 3, in the patient's body.

In an alternative embodiment represented in FIG. 5*d*, the plate 2*c* has a single opening comprising two notches as described above (see FIG. 5*c*). In an embodiment not shown, the plate may comprise a sufficient number of openings and notches to be able to assemble the plate to more than two implants.

It is clear that these different types of openings, which are either through apertures or have a wider part, can be combined in various ways without departing from the scope of the invention.

In the same way, the position of the joining part 20 can vary and be offset along the length of the plate, so as to leave the clearance required for the plate to slide during positioning. In a preferential embodiment, said position is slightly offset with respect to the center of the plate, so as to be able to slide the plate sufficiently in the first implant 1; FIG. 1*b*, to be able to have the second implant 1*a* inserted into it.

It is necessary to understand here that the device described can equally well comprise any other combination of different alternative embodiments of plates and alternative embodiments of implants without departing from the scope of the invention.

FIGS. 1*a*, 1*b*, and 1*c* illustrate different steps in the positioning of the plate 2 in two implants 1, 1*a*, in the preferential embodiment. This positioning is carried out after the implants have already been screwed into the spine, and where the attachment structures, in this case the plate support 3 and the nut 4 have already been assembled on the implant but not yet fully clamped.

In this way, in FIG. 1*a*, a first end 21 of the plate 2 is first mated with the attachment structure of the first implant 1, on the plate support 3 and under the nut 4, straddled around the clamping support 12.

Once this first end 21 has been inserted, due to the fact that the bars have a substantially constant gap, it is possible to slide the plate in the attachment structure of the first implant 1 until the second end 22 of the plate can be aligned (FIG. 1*b*) in front of the attachment structure of the second implant 1*a*.

By sliding the plate in the opposite direction, it is then possible to insert (FIG. 1*c*) said second end 22 in a similar manner in the structure of the second implant 1*a*. It is them possible to adjust the definitive position of the plate 2 and tighten the nut of the attachment structure of each of the two implants, and thus stiffen the assembly.

In this way, it is clear that it is possible to prepare the osteosynthesis device in advance using the preassembly method, comprising the following steps: assembly of the plate support 3 around the clamping support; and assembly of the nut 4 on the threading 123 of the clamping support.

Figure 6:
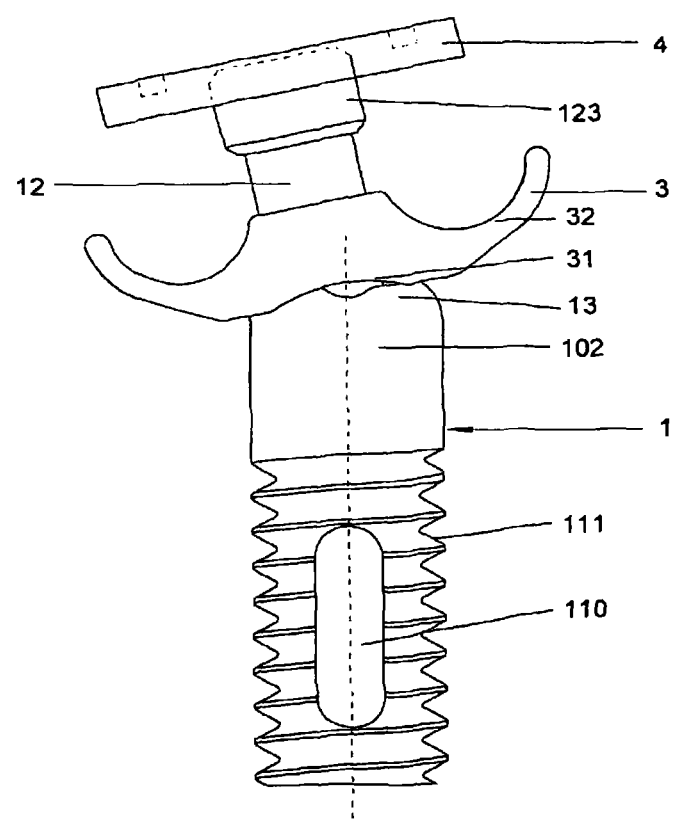
FIG. 6 represents a side view of an implant of the preassembled device according to the invention, in an embodiment comprising an inclinable clamping support and a rehabitable hollow screw with two oblong holes.

Once it has been preassembled using this method, an implant 1 of the device according to the invention can be used directly during the surgical operation, as represented in FIG. 6.

The osteosynthesis device can then be positioned using the following steps: the implants are screwed into the spine, without inserting them to their final depth. This approach position makes it possible not to be hindered by any osteophytes when positioning the plate 2. The plate 2 is inserted via a first end 21 into a first implant 1. It is then slid into said first implant to be presented in front of the attachment structure of the second implant 1*a*. The second end 22 is then inserted into the second implant. This positioning is illustrated in FIGS. 1*a*, 1*b*, and 1*c*.

At this stage and subsequently, the clearance of the plate support 3 around the clamping support 12 allows the angular and lateral movements required for insertion. This clearance also makes it possible to compensate for any alignment defects between the two implants 1, 1*a*, and thus renders the positioning of the plate 2 less delicate. The screwing of the two implants into the spine is then completed until they are clamped in their final desired position. This screwing is performed (FIG. 3) using a tool of known type, such as, for example, drive tool 51 shown in FIGS. 2 and 3, rotating the implant by means of a rotation of the clamping support 12. Since the plate 2 is already in position and held in place by the attachment structure of the implants, this additional screwing of the implants drives the plate to its desired final position close to the spine. Therefore, this driving obtained by screwing the implants makes it possible to reduce the size determined by said plate, by tightening or inlaying said plate firmly and easily on the surface of the spine. Once the implants have been completely screwed on, the plate is locked in the attachment structure of the implants, by clamping (FIG. 4) their nut 4 on the plate 2 itself resting on the plate support 3 which rests on the shoulder or on the screw head 102 of the implant. Naturally, said clamping may be carried out using other parts not mentioned, such as washers or locking devices of known types.

It must be clear to those skilled in the art that the present invention enables other embodiments in numerous other specific forms without leaving the scope of the invention as claimed. As a result, the present embodiments must be considered as illustrations, but may be modified in the field defined by the scope of the fixed claims, and the invention must not be restricted to the details given above.

The invention claimed is:

1. An implant for securing a spinal stabilization bar to a vertebra, the implant comprising:
    a bone screw having a longitudinal screw axis and comprising a bone penetration end disposed at a first end of the longitudinal screw axis and a protrusion end disposed at a second end of the longitudinal screw axis distal from the bone penetration end;
    a clamping head having a longitudinal clamping head axis and comprising
        a drive coupler disposed at a second end of the longitudinal clamping head axis and configured for engagement with a drive tool to impart rotation to the bone screw, and
        a stabilization bar support configured to receive a stabilization bar from the side of the implant; and
    a universal joint coupling the bone screw and the clamping head.

2. The implant of claim 1, in which the bone screw further comprises a threaded portion disposed along an external surface of the bone screw and configured for screwing into a bone.

3. The implant of claim 1, in which the bone screw further comprises a threaded portion disposed along a hollow core that has a bone-fusion opening.

4. The implant of claim 1, in which the stabilization bar support comprises a partially cylindrical surface complementary to a cylindrical surface of a stabilization bar.

5. The implant of claim 1, in which universal joint is configured for transmission of a rotation of the clamping head around its longitudinal clamping head axis imparted at the drive coupler to a rotation of the bone screw around its longitudinal screw axis while an angle between the longitudinal clamping head axis and the longitudinal screw axis is non-zero, and the stabilization bar support is configured to permit said transmission while the bar is attached to the implant.

6. The implant of claim 1, in which the drive coupler comprises a hexagonal recess.

7. The implant of claim 1, in which the stabilization bar support comprises an opening configured for rotatable disposition of the stabilization bar support about the longitudinal clamping head axis.

8. The implant of claim 1, in which the stabilization bar support and the protrusion end have complementary surfaces configured for support of the stabilization bar support by the protrusion end.

9. The implant of claim 8, in which the complementary surfaces are partially spherical.

10. The implant of claim 1, in which the protrusion end comprises a housing, and the protrusion end has a projection configured to prevent rotation, relative to the bone screw, of the clamping head around its longitudinal clamping head axis.

11. The implant of claim 1, in which the stabilization bar support is rotatable around the longitudinal clamping head axis.

12. A system for spinal stabilization comprising:
    a spinal stabilization bar;
    an elongated bone screw having a longitudinal screw axis;
    a clamping head having a longitudinal clamping head axis;
    a universal joint coupling the bone screw and the clamping head configured for transmission of a rotation of the clamping head around its longitudinal clamping head axis to a rotation of the bone screw around its longitudinal screw axis while an angle between the longitudinal clamping head axis and the longitudinal screw axis is non-zero; and
    a rotatable stabilization bar support configured to permit said transmission while the stabilization bar is attached to the implant.

13. The implant of claim 12, in which the stabilization bar support is rotatable around the longitudinal clamping head axis.

14. The implant of claim 13, in which the bone screw further comprises a threaded portion disposed along a hollow core that has a bone-fusion opening.

15. The implant of claim 14, in which the stabilization bar support comprises a partially cylindrical surface complementary to a cylindrical surface of the stabilization bar.

16. The implant of claim 15, in which the stabilization bar support and an end of the bone screw have complementary surfaces configured for support of the stabilization bar support by the end of the bone screw.

17. A system for spinal stabilization comprising:
    a plurality of implants each comprising:
        an elongated bone screw having a longitudinal screw axis,
        a clamping head having a longitudinal clamping head axis,
        a universal joint coupling the bone screw and the clamping head configured for transmission of a rotation of the clamping head around its longitudinal clamping head axis to a rotation of the bone screw around its longitudinal screw axis while an angle between the longitudinal clamping head axis and the longitudinal screw axis is non-zero, a rotatable stabilization bar support configured to receive a stabilization bar and permit said transmission while the bar is attached to the implant; and an elongated stabilization bar having a first distal end and a second distal end.

18. The system of claim 17, in which the stabilization bar support is configured to allow the stabilization bar to slide laterally across the stabilization bar support.

19. The system of claim 18, in which stabilization bar support is rotatable about the clamping head with the stabilization bar received in the stabilization bar support.

20. The system of claim 19, in which at least one of the implants has a housing in an end of the bone screw in which an end of the clamping head is disposable, and that end of the clamping head has a projection configured to cooperate with a concave portion of the housing to prevent rotation, relative to the bone screw, of the clamping head around the longitudinal clamping head axis.

\* \* \* \* \*